(12) United States Patent
Klemer

(10) Patent No.: US 12,031,889 B1
(45) Date of Patent: Jul. 9, 2024

(54) APPARATUS FOR TISSUE LYSIS UNDER ELECTROMAGNETIC FIELD CONTROL

(71) Applicant: K2 Biomicrosystems LLC, Geneva, IL (US)

(72) Inventor: David P. Klemer, Geneva, IL (US)

(73) Assignee: K2 Biomicrosystems LLC, Geneva, IL (US)

( * ) Notice: Subject to any disclaimer, the term of this patent is extended or adjusted under 35 U.S.C. 154(b) by 652 days.

(21) Appl. No.: 16/876,562

(22) Filed: May 18, 2020

Related U.S. Application Data

(60) Provisional application No. 62/849,620, filed on May 17, 2019.

(51) Int. Cl.

| | |
|---|---|
| *C12N 13/00* | (2006.01) |
| *B01L 3/00* | (2006.01) |
| *C12M 1/00* | (2006.01) |
| *C12N 1/06* | (2006.01) |
| *C12N 15/10* | (2006.01) |
| *G01N 1/28* | (2006.01) |
| *G01N 1/40* | (2006.01) |
| *G01N 27/447* | (2006.01) |

(52) U.S. Cl.
CPC .............. *G01N 1/286* (2013.01); *B01L 3/508* (2013.01); *C12M 47/06* (2013.01); *C12N 1/06* (2013.01); *C12N 1/066* (2013.01); *C12N 13/00* (2013.01); *C12N 15/10* (2013.01); *C12N 15/1003* (2013.01); *G01N 1/4077* (2013.01); *G01N 27/44786* (2013.01); *B01L 2400/043* (2013.01)

(58) Field of Classification Search
None
See application file for complete search history.

(56) References Cited

U.S. PATENT DOCUMENTS

| | | | | |
|---|---|---|---|---|
| 4,906,576 | A | * | 3/1990 | Marshall, III ........... C12N 5/12 435/173.9 |
| 5,428,451 | A | * | 6/1995 | Lea ....................... G01N 15/147 356/417 |
| 2002/0036142 | A1 | * | 3/2002 | Gascoyne ............... B03C 5/028 204/547 |
| 2002/0185557 | A1 | * | 12/2002 | Sparks ................... C12M 47/06 241/1 |
| 2004/0001780 | A1 | * | 1/2004 | Schirr ................. B01L 3/50851 422/400 |
| 2010/0068781 | A1 | * | 3/2010 | Rajagopal .............. C12N 13/00 435/306.1 |

* cited by examiner

*Primary Examiner* — Neil N Turk
(74) *Attorney, Agent, or Firm* — Boyle Fredrickson, S.C.

(57) ABSTRACT

The present invention relates generally to the process of biological tissue and/or cellular disruption, and more particularly to an apparatus which can achieve such tissue and/or cellular disruption through the imposition of a time-varying electromagnetic field generated by electrical means and used to direct magnetic beads or other magnetic particles against a tissue sample. Tissue disruption is accomplished through mechanical impact between the magnetic particles and the sample biological tissue.

18 Claims, 8 Drawing Sheets

APPARATUS FOR TISSUE LYSIS UNDER ELECTROMAGNETIC FIELD CONTROL

CROSS REFERENCE TO RELATED APPLICATION

This application claims priority to U.S. Provisional Patent Application Ser. No. 62/849,620 filed on May 17, 2019, the entirety of which is incorporated herein by reference.

GOVERNMENT LICENSED RIGHTS

This invention was made with government support under grant number 2017-33610-26738 awarded by the U.S. Department of Agriculture, National Institute of Food and Agriculture. The government has certain rights in the invention. iEdison Reference: EIR Number 10034827-19-0001 and iEdison Docket Number 19-0001.

BACKGROUND OF INVENTION

1. Field of the Invention

The present invention relates to the field of biological tissue sample preparation designed to release biologically relevant microorganisms, organelles, and/or organic molecules for subsequent analysis, accomplished through lysis of cellular or interstitial tissue structures. More particularly, the subject invention concerns an apparatus designed to mechanically disrupt such cellular or interstitial tissue structures, in which magnetically-susceptible lysing beads are steered and accelerated against tissue samples by externally-imposed magnetic fields generated electromagnetically.

2. Discussion of the Related Art

In many applications in biology, agriculture, human medicine, pharmacology, veterinary sciences, infectious disease diagnosis, and life sciences in general, it is often helpful to isolate, detect and quantify organic molecules (including proteins, nucleic acids, carbohydrates and/or lipid molecules), structural molecules, and/or microorganisms (such as bacteria, viruses, fungi, protozoa, and others). Identification of these molecules or organisms is potentially more difficult if such molecules or organisms are isolated within cellular compartments and/or tissue compartments which render them inaccessible, making extraction and isolation difficult. Microorganisms such as viruses and bacteria so isolated may remain dormant inside of cells, frustrating attempts at extraction, detection, identification and/or quantification. A typical example is the causative agent of tuberculosis, the bacterium *Mycobacterium tuberculosis*, which may remain dormant and viable within cells of the lung for many years within a subcompartment ("phagosome") of a lung cell.

Likewise, organic molecules which are specific to microorganisms (such as specific receptor proteins and nucleic acid sequences) may also be rendered inaccessible if they remain isolated within cellular or tissue compartments. Reagents and techniques for successful biochemical extraction of organic molecules are well-established, and commercial products are available for this purpose. However, in many cases chemical extraction protocols may be unsuccessful or only partially successful, due in part to tissue structures which serve to hinder access to such molecules and/or microorganisms—including, for example. strong and robust cell walls which further frustrate such extraction techniques. In such cases it becomes necessary to augment biochemical means of isolation and extraction with other techniques, including mechanical techniques to disrupt tissue structures which frustrate successful extraction.

Before discussing these other techniques (including mechanical techniques), it is helpful to review the ultimate objective for isolation of organic molecules in various fields of science and technology. One major organic molecule of relevant interest consists of a sequence of nucleotides assembled into a polymeric structure, so-called nucleic acids. A nucleotide is defined as an organic molecule which typically consists of atoms of carbon, hydrogen, oxygen, nitrogen and phosphorus arranged in such a way to form a base unit which can be linked together to form long molecular chains. Examples of these fundamental nucleotide units are adenine, cytosine, guanine, thymine and uracil—typically abbreviated as A, C, T, G and U, respectively—which link together in a polymeric chain to form nucleic acids. Depending on the specific atomic composition of the underlying chain, such nucleic acids may be referred to respectively as deoxyribonucleic acid (DNA), ribonucleic acid (RNA) or other variants, such as messenger RNA (mRNA), transfer RNA (tRNA), and other variant forms.

The particular sequence of fundamental nucleotide units forming a complete nucleic acid molecule may be specific to a given biological organism. Accordingly, there is great interest in extracting nucleic acids from organisms in various fields of science and analyzing said extracted nucleic acids to, for example, identify a specific strain of bacteria, identify an organism's susceptibility to disease, identify evolutionary relationships between similar organisms, and numerous other purposes. Extraction is an important initial step in subsequent processing of nucleic acids; such subsequent processing steps may include sequencing of the underlying nucleotide structure, quantification of the concentration of nucleic acids within a tissue sample, increasing the concentration of nucleic acid molecules through amplification protocols, and many other types of processing.

Extraction is thus clearly a fundamental and important processing step in many fields of natural science in which nucleic acids play an important role. The above considerations also apply to other types of organic molecules which reside inside living organisms—for example proteins, also formed as polymeric chains of fundamental organic building blocks referred to as amino acids.

As discussed in the paragraphs above, chemical methods may be used to extract biomolecules of interest from tissues and cells. As an example, in the extraction of DNA chemical reagents are typically used sequentially to first disrupt the membrane surrounding a biological cell, degrade (i.e., break down or hydrolyze) cellular proteins which may be present, and isolate the remaining nucleic acids associated with the cell.

In many cases, such as with human cells which are easily gathered, these chemical processes may work satisfactorily to isolate and extract DNA. However, in other important instances—such as with various types of plant tissue—simple chemical processing is inadequate for extraction of microorganisms (e.g., bacteria) and/or biomolecules of interest, due to the presence of additional structures which form relatively impenetrable layers surrounding a biological cell. Such secondary layers may serve to impose rigidity and/or act as a waterproofing layer atop the primary wall surrounding the cell. Additional polymeric organic molecules such as cellulose and lignin may further serve to frustrate attempts to isolate biomolecules of interest using purely chemical means.

As a result, it oftentimes becomes necessary to apply mechanical means to further disrupt tissue and/or cellular structures during the extraction process in order to more effectively isolate relevant biomolecules such as DNA. Instrumentation is commercially available (e.g., FastPrep-24 homogenizer by MPBiomedicals) to accomplish this disruption, but such instrumentation suffers from numerous disadvantages, including a large electrical power requirement (i.e., need for access to a line (110 VAC) source of electrical power), significant weight, and high cost. In addition, such instrumentation typically employs powerful motors to physically shake a sample tube in a process which involves numerous moving parts; these considerations can ultimately impact the usable lifespan and long-term reliability of the instrumentation.

Based on the aforementioned considerations, it is thus desirable to have an instrument which can achieve tissue and/or cellular disruption in a compact, portable and lightweight platform. In addition to addressing the disadvantages just described, such a platform would further facilitate the ability to extract and isolate biomolecules, microorganisms and/or other components from tissue samples in remote field settings without access to standard sources of AC electrical power.

Furthermore, it is desirable to have an instrument construction which has no physically moving parts apart from the contents within a sample tube, in order to achieve higher long-term reliability. This construction may have the added benefit of lower audible noise and vibration, a useful and desirable advantage in conventional laboratory settings.

SUMMARY OF THE INVENTION

The subject matter disclosed herein provides an apparatus which achieves tissue and/or cellular disruption through the use of time-varying electromagnetic fields which are generated by electronic means and used to direct magnetic beads or other magnetic particles against a tissue sample enclosed in a sample tube or container. Along with tissue samples placed within the sample container, one or more magnetic beads or particles are also included, and the sample tube with enclosed tissue sample is inserted into a tissue sample chamber of the apparatus, within or in close proximity to low-resistivity electromagnetic coils used to generate electromagnetic fields. Activation of a control processor is used to direct a waveform generating circuit and/or switching circuit, which in turn imposes time-varying electrical currents on the low-resistivity electromagnetic coils so as to generate the aforementioned fields. The low-resistivity electromagnetic coils are designed such that pulsatile currents in the range of tens to hundreds of amperes may be imposed on the coils in a time-varying fashion while ensuring that the ambient temperature in the vicinity of the coil does not increase significantly (i.e., more than one degree Celsius). The magnetic fields produced by the time-varying currents act upon the magnetic beads and/or particles contained within the sample tube, imposing motive forces which result from interactions with the electromagnetic fields. Appropriate design of the coil and the time-varying currents results in forces which are significant in magnitude, and which result in physical motion of the magnetic beads/particles. As a result, the magnetic beads/particles are steered and accelerated against tissue samples within the sample tube, achieving tissue disruption through mechanical impact between the magnetic particles and the tissue.

The incorporation of a waveform generating circuit allows for the definition of complex time-varying, pulsatile voltage and current waveforms which vary in amplitude as time proceeds. When applied to the electromagnetic coils, such complex waveforms may be used to generate complex time-varying electromagnetic fields having magnitudes in the range 500 to 50,000 gauss (or equivalently 0.05 to 5 tesla). This allows the present invention to modulate and control the forces created at the moment of mechanical impact between the magnetic particles and the sample tissue, resulting in optimal and effective tissue disruption The present invention also includes the possibility of sensor devices placed in proximity to the electromagnetic coils and/or sample tube. Such sensor devices may consist of, for example, electromagnetic field sensors (including, for example, semiconductor Hall-effect sensors and/or additional electromagnetic coils which serve to detect and quantify the presence of local varying magnetic fields), vibration sensors and temperature sensors. These sensors may be used to provide information on the instantaneous magnitude of the time-varying electromagnetic fields generated by the coils and/or the magnitude of the resulting mechanical forces between the magnetic particles and the sample tissue within the sample tube. This information may then be used as a feedback signal to control and define the time-varying waveforms generated by the waveform generating circuit, so as to optimize the effectiveness of the tissue disruption.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION

Figure 1:
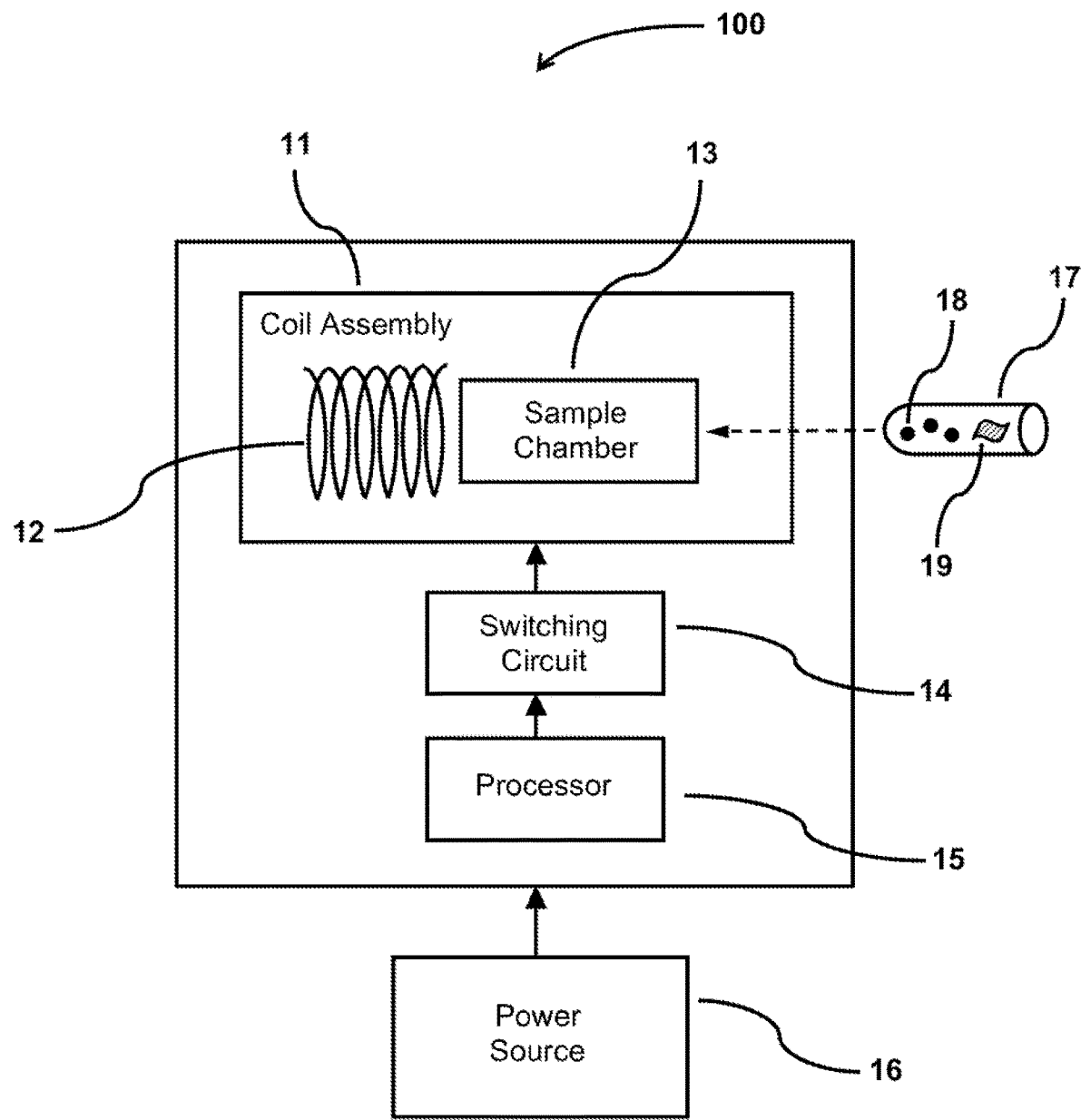
FIG. 1 illustrates a block diagram of an exemplary embodiment of an apparatus which is capable of tissue lysis via electromagnetic field control.

For the purpose of promoting an understanding of the present invention, references are made in the text to exemplary embodiments of an apparatus designed to mechanically disrupt such cellular or interstitial tissue structures, in which magnetically-susceptible lysing objects are steered and accelerated against tissue samples by externally-imposed magnetic fields generated electromagnetically, only some of which are described herein. It should be understood that no limitations on the scope of the invention are intended by describing these exemplary embodiments. In some embodiments, the assemblies include a sampling chamber. The assemblies may also comprise a toroidal sampling chamber. Also disclosed herein are methods of processing tissue samples and methods of administering tissue lysis under electromagnetic field control to a tissue sample. The disclosed methods can include preparing and/or obtaining tissue lysis of a sample. Various features of the apparatus for tissue lysis as are disclosed herein may be grouped together in a single embodiment, figure, or description thereof for the purpose of streamlining the disclosure. Many of these features may be used alone and/or in combination with one another in the various embodiments.

One of ordinary skill in the art will readily appreciate that alternate but functionally equivalent components, materials, and layouts may be used. The inclusion of additional elements may be deemed readily apparent to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the assembly is not intended to limit the scope of the disclosure but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

Moreover, the terms "substantially" or "approximately" as used herein may be applied to modify any quantitative representation that could permissibly vary without resulting in a change in the basic function to which it is related.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other.

As used herein, the term "tissue sample" refers to a quantity of biological material composed of cellular or sub-cellular components extracted from a prokaryotic or eukaryotic organism, or other cellular or sub-cellular material, which may potentially contain one or more of the following: subcellular organelles, organic molecules (such as proteins, nucleic acids, carbohydrates and/or lipid molecules), structural components such as cell wall, polymeric organic molecules, and/or microorganisms which may possibly be foreign to the aforementioned organism and which may also themselves contain similar cellular or subcellular material.

As used herein, the term "tissue sample chamber" refers to a receptacle structurally capable of holding or containing a sample container or other removable vessel which contains a tissue sample and which facilitates insertion and removal of said tissue sample from said tissue sample chamber. In the following, the term "sample tube" may be used synonymously as "sample container."

As used herein, the term "magnetic field" refers to a field which is described by a magnitude (or strength) and direction in space, capable of imposing a physical force on certain materials when said materials are proximate said magnetic field.

As used herein, the term "magnetic material" refers to a material which experiences a directional motive force when placed within a magnetic field. Such materials may be categorized as ferromagnetic, ferrimagnetic, paramagnetic, diamagnetic, or antiferromagnetic, depending on the magnitude and/or direction of the response of the material to said magnetic field. The separate and mutually-exclusive category of non-magnetic materials refers to materials which experience no motive force when placed within a magnetic field. A "magnetic particle" is used to refer to an object which is composed entirely or in part of said magnetic material. The term "magnetic bead" may be used interchangeably with the term magnetic particle, although "magnetic bead" is typically reserved for the subset of magnetic particles which are roughly spherical in shape.

As used herein, an "electromagnetic coil" is an electrical conductor (such as a metallic wire) which is arranged in the shape of a helix and which generates a magnetic field when an electric current is established in said coil. In particular, a "solenoidal coil" is an electromagnetic coil in which the helix is formed about a linear axis.

As used herein, the term "low-resistivity electromagnetic coil" refers to an electromagnetic coil formed using an electrical conductor having an electrical resistivity (measured in ohm-meters) and conductor cross-section which results in minimal Joule heating. For example in one non-limiting embodiment the coil exhibits heating of 1 degree Celsius or less, when subjected to large electrical currents, 10 amperes or greater, for a brief period of time 20 milliseconds or less, either as a single current pulse, or as a pulse train having a duty cycle of 40% or less. Such a coil may be formed from electrically conductive metallic wire, or other electrically conductive materials such as superconducting materials.

As used herein, the term "modulator" refers to a component which may cause the amplitude, intensity, frequency, or other property of a magnetic field or other signal to vary over time.

As used herein, a "toroidal sample container" refers to a sample container having an internal volume defined as a volume of revolution of a closed two-dimensional cross-sectional shape, as described below and illustrated in FIG. 6.

As used herein, a "generalized toroidal sample container" refers to a toroidal sample container which is deformed in such a way that the circumferential axis internal to the container assumes a shape other than that of a circle. For example, if the circumferential axis of the sample container is elliptical in shape, while the sample container cross section perpendicular to the circumferential axis remains circular in shape, the sample container would be referred to as an elliptic toroidal sample container.

Turning now to the Figures, FIG. 1 illustrates a block diagram of an exemplary embodiment of apparatus for tissue lysis under electromagnetic field control 100. Tissue lysis apparatus comprises low-resistivity electromagnetic coil assembly 11 which comprises one or more low-resistivity electromagnetic coils 12, sample chamber 13, switching circuit 14, processor 15 and power source 16. Also illustrated in FIG. 1 is a typical sample container or sample tube 17, which may be formed from a test tube, PCR tube, cuvette, or the like, containing tissue sample 19 and one or more magnetic beads 18; said sample tube is placed within sample chamber 13, located proximate low-resistivity electromagnetic coil 12 within coil assembly 11. Time varying magnetic fields generated by said electromagnetic coil produce motive forces on magnetic beads 18 placed within sample tube 17, as described above.

In the embodiment shown, processor 15 generates a time-varying control signal which is used to trigger switching circuit 14, allowing pulsatile electrical currents to flow in low-resistivity electromagnetic coil 12 within coil assembly 11. Power source 16 provides a voltage sufficient to generate said electrical currents. In one nonlimiting embodiment of the present invention, application of pulsatile currents to the coils results in time-varying magnetic fields in the range of approximately 500 to 50,000 gauss in the vicinity of said coils, producing motive forces on magnetic beads 18 and forcibly directing them against tissue sample 19. The magnetic bead 18 may be formed generally of magnetic particle that are placed within the sample container, and may include one or more of: permanently-magnetized magnetic particles, ferromagnetic particles, paramagnetic particles, diamagnetic particles, iron oxide nanoparticles, or other particles experiencing a motive force upon influence by an electromagnetic field.

Figure 2:
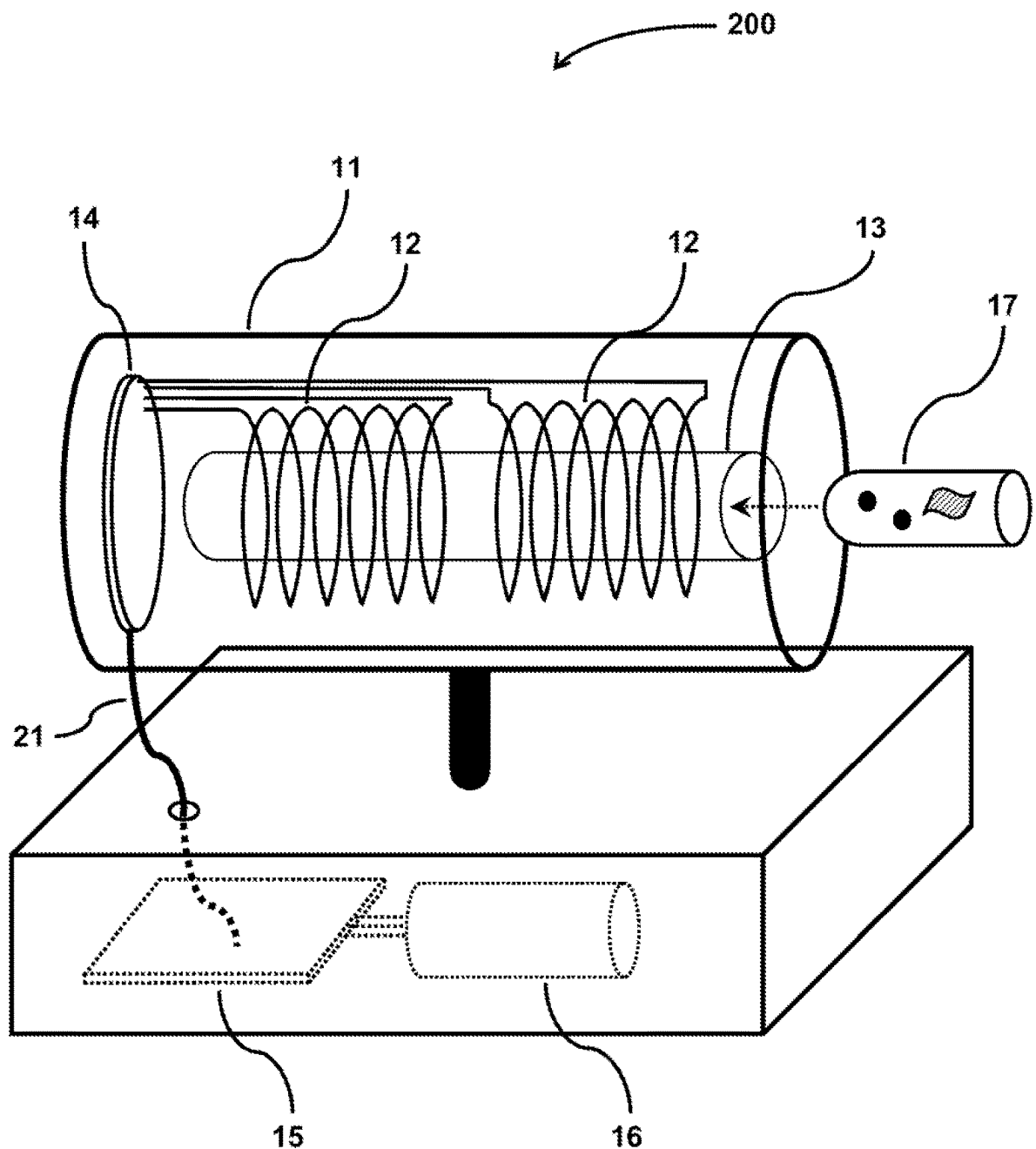
FIG. 2 is an illustration of an exemplary physical embodiment of an apparatus which is capable of tissue lysis via electromagnetic field control, viewed from the side.

FIG. 2 illustrates an exemplary physical embodiment of an instrument which incorporates the elements of an apparatus for tissue lysis under electromagnetic field control 200. In this embodiment, coil assembly 11 consists of two low-resistivity electromagnetic coils 12 arranged side-by-side and controlled by switching circuit 14. Sample tube 17 is placed within an accessible sample chamber 13 positioned within a hollow bore aligned with the longitudinal axis of said coils. Processor 15 and power source 16 are placed within a separate housing and connected to coil assembly 11 by electrical cable 21.

Figure 3:
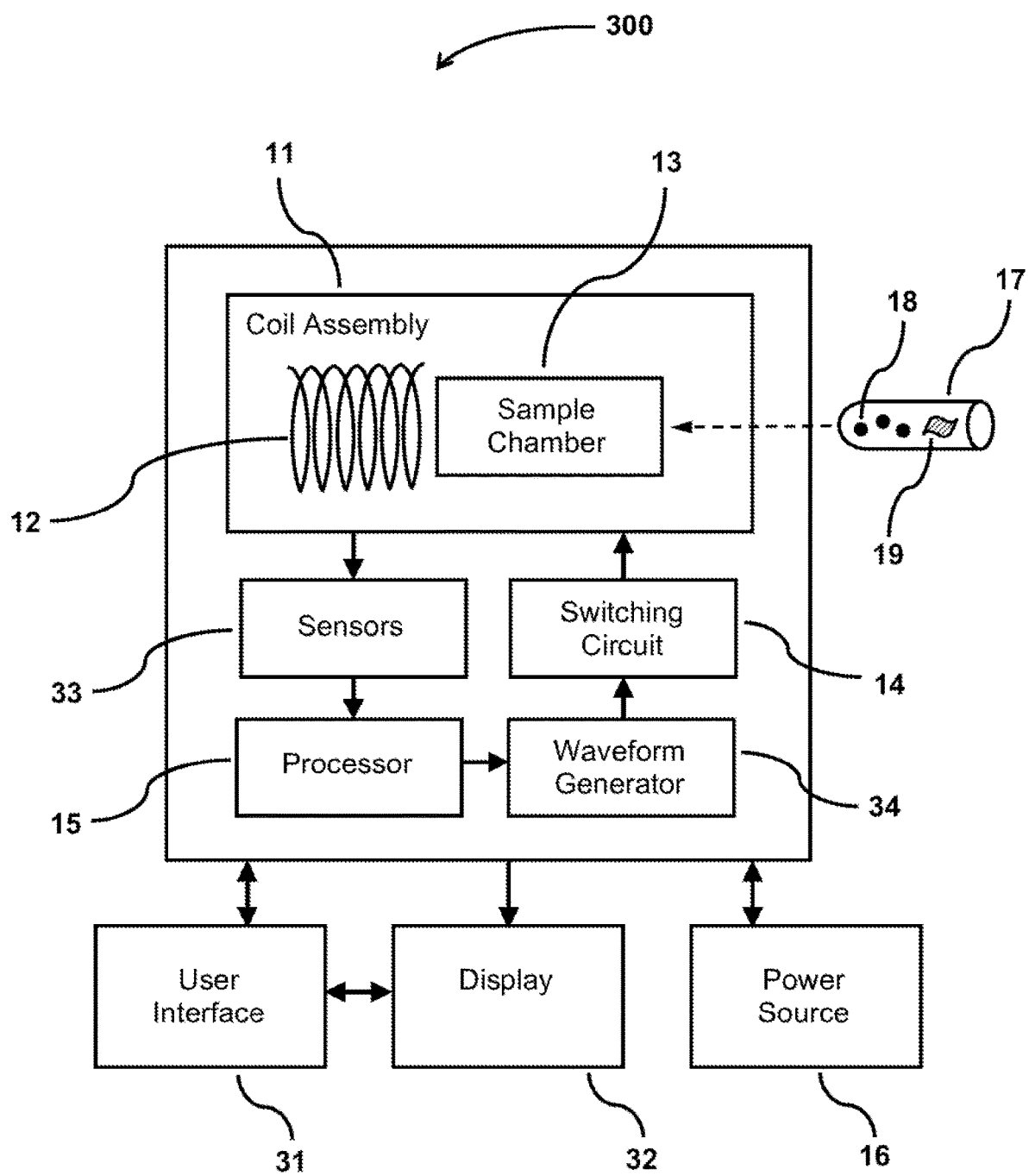
FIG. 3 illustrates a block diagram of an alternate exemplary embodiment of an apparatus which is capable of tissue lysis via electromagnetic field control.

FIG. 3 illustrates a block diagram of an alternate exemplary embodiment of apparatus for tissue lysis under electromagnetic field control 300. In this embodiment, the apparatus of FIG. 1 is augmented by user interface 31 and instrument display 32 which permit the user to view and adjust parameters stored within processor 15 and which define the shape of the time-varying pulsatile current waveform applied to low-resistivity electromagnetic coil 12 within coil assembly 11. The shape of the pulsatile current waveform in turn determines the duration and magnitude of the magnetic fields generated within the sample tube. One or more sensors 33 are used to measure and quantify various quantifications of physical parameters of interest proximate to sample tube 17. In such an embodiment, the sensors 33 may be formed of one or more of a solid-state magnetic field sensor, a Hall-effect sensor, a piezoelectric sensor, a vibration sensor, a temperature sensor, or an electromagnetic sensing coil. These parameters that are detected and quantifiably measured by the sensor 33 may include, but are not limited to, local instantaneous temperature, local instantaneous magnetic field strength and direction, and vibration associated with motion of magnetic beads within the sample tube. In this embodiment, processor 15 is used to control a separate waveform generator 34 which produces a predefined time-varying signal for triggering switching circuit 14. That is to say, that the waveform generator 34 interposed between said processor 15 and said switching circuit 14 is operable to provide the switching circuit 14 with a prescribed time-varying waveform signal upon direction by said processor 15 where the time-varying waveform signal may be one of: a square waveform, a sinusoidal waveform, a pulse waveform with fixed duty cycle, a pulse waveform with duty cycle varying over time, a pseudo-random pulse waveform, or a time-varying waveform consisting of a superposition of sinusoidal waveforms each of which having a unique frequency. The apparatus may further include a user interface that is operable for entry of operating parameters to the processors 15, and thereby the waveform generator 34, switching circuit 14 and/or the sensors 33

Figure 4:
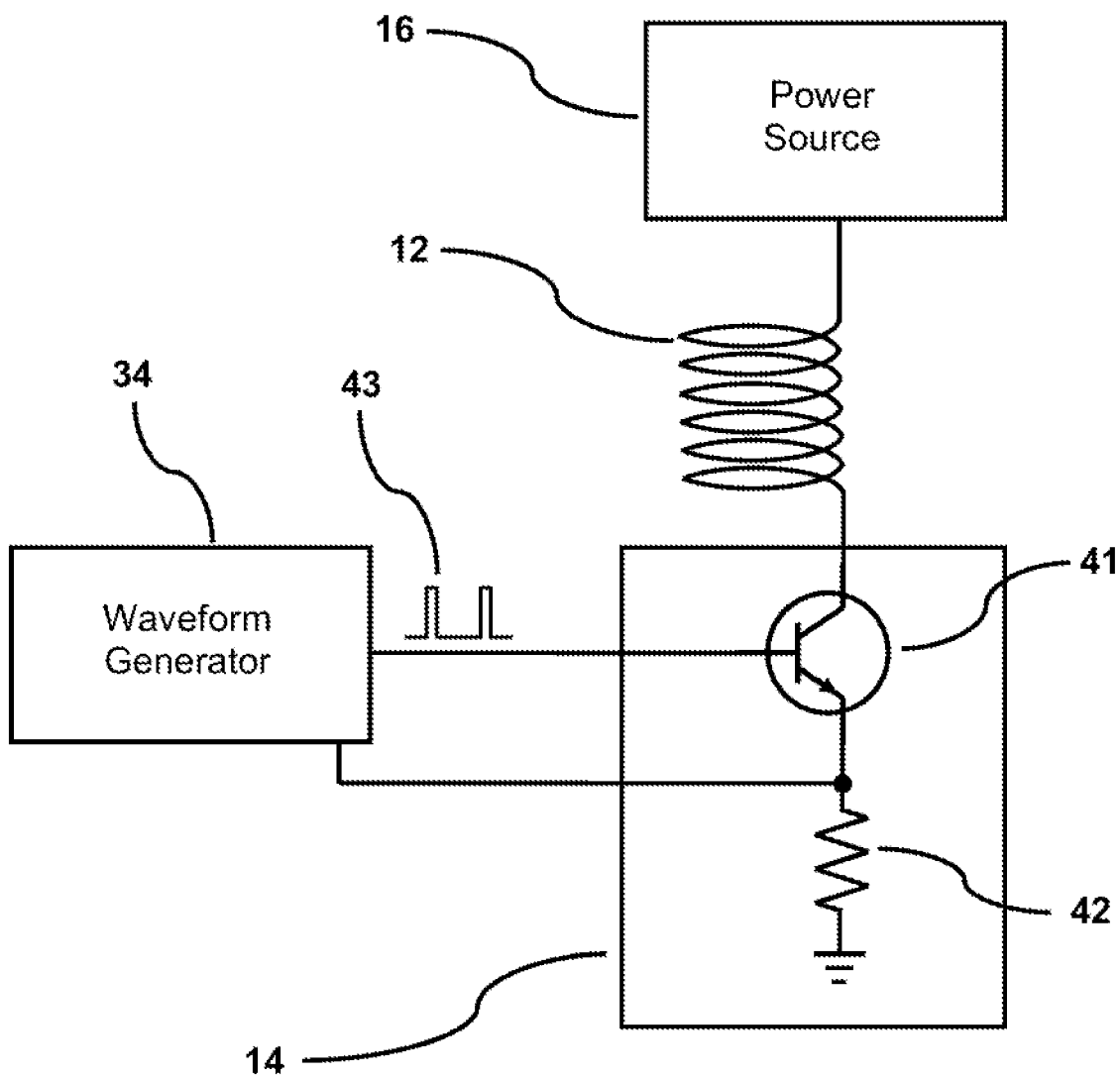
FIG. 4 is a schematic illustration of an exemplary switching circuit incorporated into an apparatus which is capable of tissue lysis via electromagnetic field control.

FIG. 4 presents an exemplary schematic illustration of switching circuit 14 controlled by waveform generator 34. In this embodiment, switching device 41 consists of a semiconductor transistor which controls the electrical voltage and current waveform imposed upon coil 12. Power source 16 serves as the source of energy which delivers electrical current to coil 12 under the control of switching device 41. Feedback element 42 converts electrical current passing through coil 12 into a feedback voltage which is transmitted to waveform generator 34 in order to inform and adjust the time-varying signal 43 generated by waveform generator 34. In other embodiments, switching device 41 may consist of an electromechanical switch such as relay, or any of various alternative electrical switching devices such as bipolar transistor, insulated-gate bipolar transistor, field effect transistor, thyristor, silicon-controlled rectifier, or other solid-state switching device. The apparatus may further include a user interface (not shown) that is operable for entry of operating parameters to the processors 15, and thereby the waveform generator 34, switching circuit 14 and/or the sensors 33. An output (not shown) for outputting measurements and operating parameters may also be included in the apparatus, where the output may comprise one or more of a display, an audio transducer, a memory storage device, a wireless transmission link, and a connection to an external processor.

Figure 5:
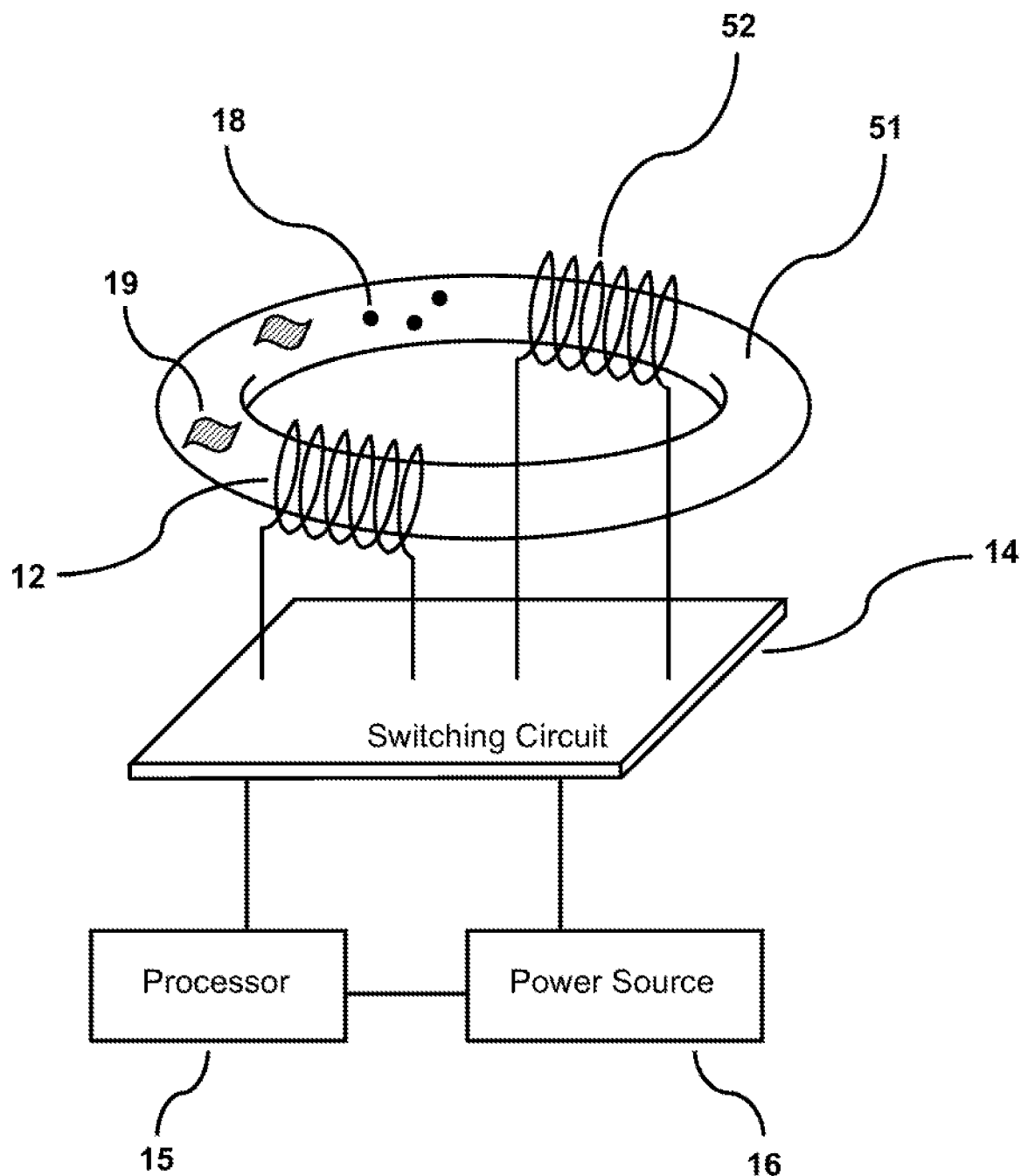
FIG. 5 illustrates an exemplary embodiment of an apparatus which is capable of tissue lysis via electromagnetic field control, in which a toroidal sample container is used to contain sample tissue and magnetic beads.

FIG. 5 illustrates an alternate exemplary embodiment of apparatus for tissue lysis under electromagnetic field control 300, in which a toroidal sample container 51 is used to contain the tissue sample 19 and magnetic beads 18. In this embodiment, one or more low-resistivity electromagnetic coils 12 are placed about the sample container such that the longitudinal axis of each electromagnetic coil 12 is roughly coincident with the circumferential axis of the toroidal sample container. In this embodiment, a second electromagnetic coil 52 may be incorporated to either generate an electromagnetic field, sense the time-varying electromagnetic fields within the sample tube, or perform either function (generation or sensing) at distinct points in time. Should second electromagnetic coil 52 be used to sense time-varying fields within the sample tube, such a coil would be referred to as a sensing coil.

Figure 6:
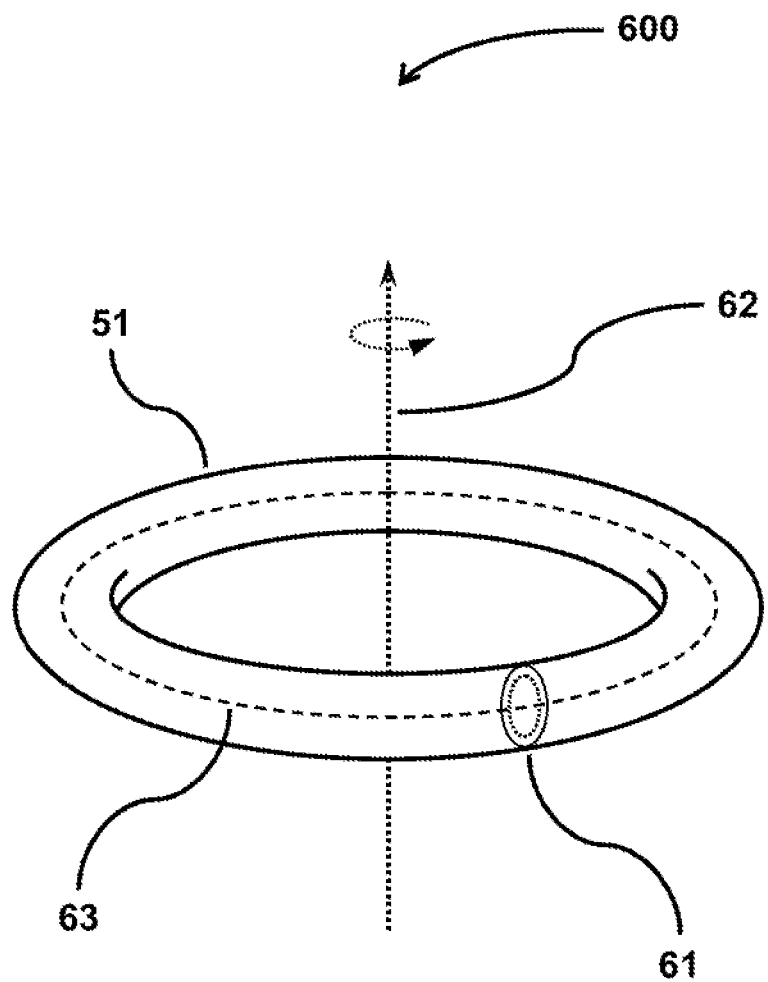
FIG. 6 illustrates an exemplary toroidal sample container and defines specific axes used in the definition of said sample container.

Toroidal sample container 51 refers to a sample container which has an internal volume formed from the volume of revolution of a closed two-dimensional cross-sectional shape 61, shown in FIG. 6. Said closed two-dimensional shape is rotated about an axis of revolution 62 which is coplanar to that of the two-dimensional shape, but lying external to the shape. If the two-dimensional shape is a circle, the sample container is referred to as a circular torus. If the two-dimensional shape is a square, the container is referred to as a square torus. A circumferential axis 63 internal to the volume of revolution is defined as the locus of all points passing through the centroid of said two-dimensional shape as it is rotated about the axis of revolution; in all cases circumferential axis 63 is a circle perpendicular to axis of revolution 62. As noted in the Glossary, in the generalized case where circumferential axis 63 is deformed to assume a shape other than that of a circle, the sample container would be referred to as a generalized toroidal sample container. For example, if circumferential axis 63 is deformed to become an ellipse, the sample container is referred to as an elliptic torus. In practice, said toroidal sample container 51 comprises two or more sub-units which are disassembled to allow for insertion of tissue sample and magnetic beads, and subsequently reassembled, or an alternative device as to provide for ingress and egress of tissue sample and magnetic beads to and from the interior toroidal sample container.

Figure 7A:
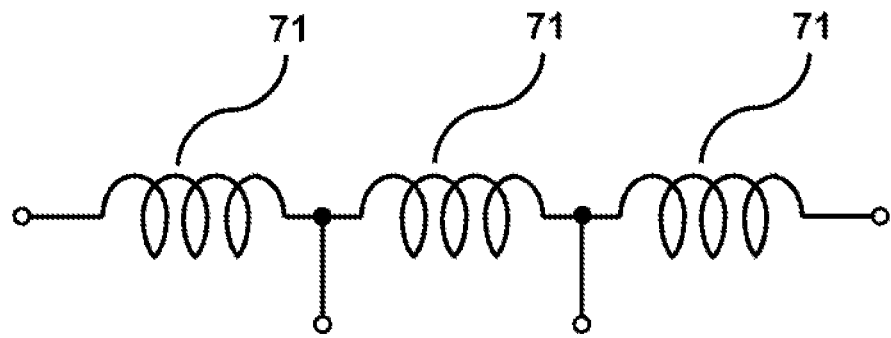
FIG. 7A illustrates an exemplary design of a low-resistivity electro-magnetic coil in which a plurality of interconnected sub-coils are spatially incorporated in a series arrangement.
Figure 7B:
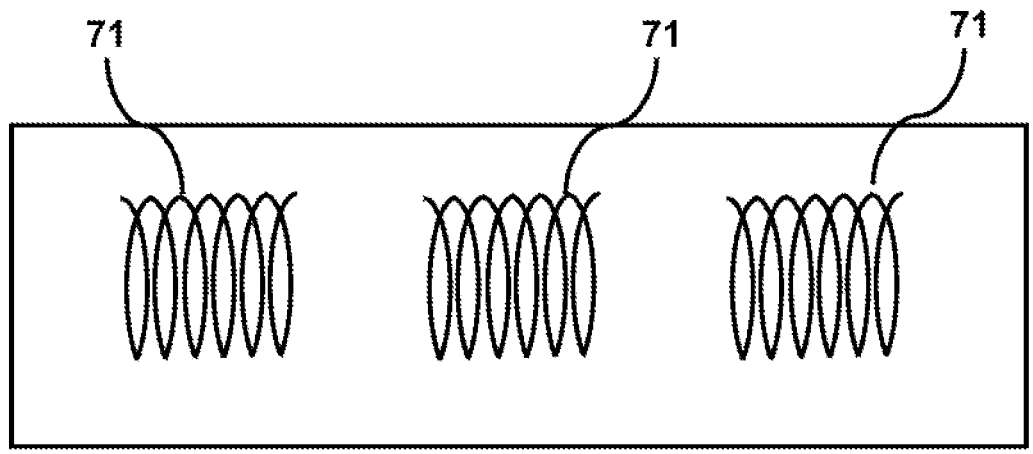
FIG. 7B illustrates an exemplary design of a low-resistivity electro-magnetic coil in which sub-coils are spatially arranged in a side-by-side manner.
Figure 7C:
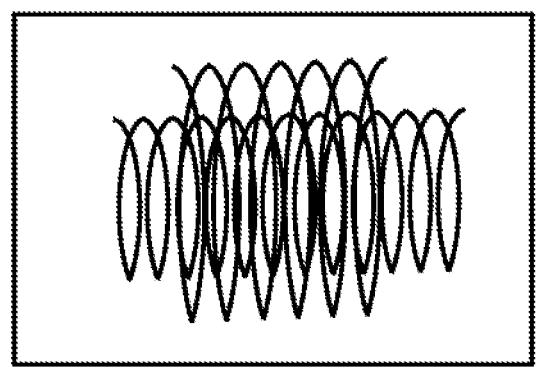
FIG. 7C illustrates an exemplary design of a low-resistivity electro-magnetic coil in which sub-coils are placed within each other; and, FIG. 8 is an illustration of an exemplary physical arrangement between a sample container (containing sample tissue and magnetic beads) and a low-resistivity electromagnetic coil, depicting lines of magnetic field which interact with the sample container and its contents.

As used herein, the low-resistivity electromagnetic coil 12 may consist of a single coil of electrically conductive material, or it may be generalized to refer to one single coil comprising a plurality of sub-coils electrically connected in series, or parallel, or combinations thereof. In such an arrangement, such sub-coils may be individually electrically accessible, and may serve to either generate electromagnetic fields, sense time-varying electromagnetic field, or serve both functions at different points in time. FIG. 7 illustrates an electromagnetic coil formed as an arrangement of three sub-coils 71 electrically connected in series (FIG. 7a), each of which is individually electrically accessible. Such sub-coils may be spatially arranged in a side-by-side manner as shown in FIG. 7b, or sub-coils may be placed within each other as shown in FIG. 7c. In the cases shown, the longitudinal axis of each sub-coil, and the longitudinal axis of the composite coil are coincident.

Figure 8:
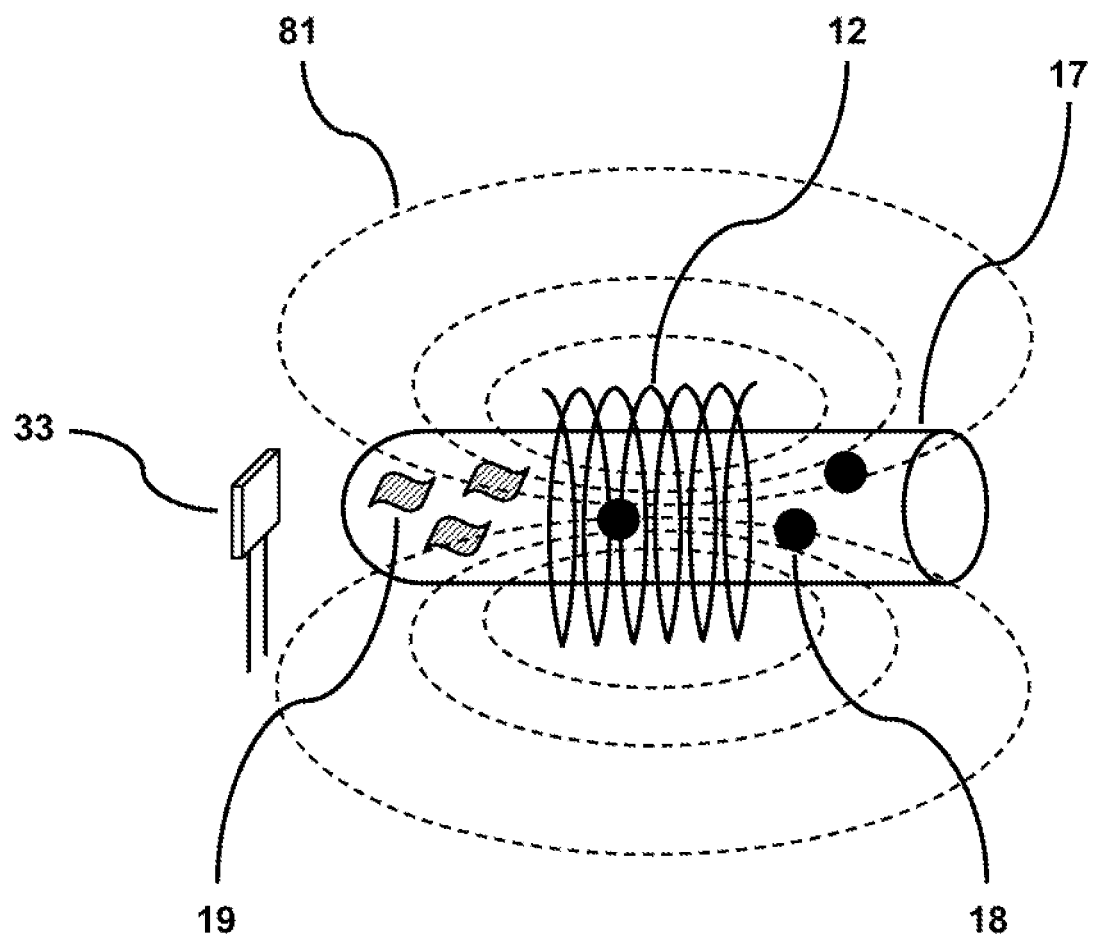

FIG. 8 illustrates the physical relationship between electromagnetic fields generated by electrical current flowing through low-resistivity electromagnetic coil 12 and sample tube 17 which is placed within coil 12 in such a manner as to intercept the magnetic fields. The electromagnetic fields are depicted as lines of magnetic field 81 passing through and about low-resistivity electromagnetic coil 12 formed as a solenoidal coil. In other embodiments, sample tube 17 may be located adjacent to and in close proximity to coil 12. In still other embodiments, the center of coil 21 may be filled with a magnetic material so as to shape or concentrate the magnetic field lines passing though and around coil 12, with sample tube 17 placed in close proximity so as to intercept the magnetic field lines.

The electromagnetic field generated by low-resistivity electromagnetic coil 12 imparts force on magnetic beads 18, resulting in physical acceleration of the bead. This in turn produces disrupting forces as a consequence of impact between magnetic bead 18 and sample tissue 19 within the sample tube. Also shown is sensor 33, used to provide information on the strength and direction of the time-varying magnetic fields, mechanical vibrations resulting from mechanical interactions between magnetic bead 18 and sample tissue 19 within sample tube 17, and/or other physical parameters.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. An apparatus for tissue lysis under electromagnetic field control comprising:
   a sample chamber suitable for accepting a sample container enclosing at least one magnetic particle along with tissue sample;
   a coil assembly arranged and configured around said sample chamber, the coil assembly comprising one or more electromagnetic coils, each of the one or more electromagnetic coils defining an outer coil surface and interior space disposed inwardly of the outer coil surface extending from a first end of the coil to an opposing second end, wherein at least a portion of the sample chamber is disposed within the interior space and extends from at least the first end to at least the second end of each coil, the one or more electromagnetic coils configured to generate a magnetic field proximate said sample chamber upon excitation by an electrical current from 10 amperes to 900 amperes while limiting a variation in an ambient temperature at the coil assembly of less than or equal to 1 degree Celsius during generation of the magnetic field;

a switching circuit comprising an electrical switching device for controlling said electrical current;

a processor electrically coupled to said switching circuit capable of activating said electrical switching device in a prescribed time-varying fashion;

a waveform generator interposed between said processor and said switching circuit, said waveform generator operable to provide said switching circuit with a prescribed time-varying current waveform upon direction by said processor, wherein said prescribed time-varying current waveform results in the magnetic field having a magnitude of 500 gauss to 50,000 gauss;

and, a power source configured to deliver electrical voltages and currents to said processor, switching circuit, waveform generator and electromagnetic coils.

2. The apparatus of claim 1 in which said waveform generator is capable of producing a time-varying signal selected from a group consisting of: a square waveform, a pulse waveform with fixed duty cycle, a pulse waveform with duty cycle varying over time, and a pseudo-random pulse waveform.

3. The apparatus of claim 1 further comprising at least one sensor component suitable for detection and quantification of physical parameters proximate said sample container, said sensor component selected from a group consisting of: a solid-state magnetic field sensor, a Hall-effect sensor, a piezoelectric sensor, a vibration sensor, and an electromagnetic sensing coil.

4. The apparatus of claim 1 further comprising a user interface in operable communication with said processor, said user interface operable for entry of operating parameters to said processor.

5. The apparatus of claim 3 further comprising an output in operable communication with said at least one sensor component, said output configured for receiving and outputting measurements from the at least one sensor component and operating parameters of said apparatus, wherein the output is selected from a group consisting of: a display, an audio transducer, a memory storage device, a wireless transmission link, and a connection to an external processor.

6. The apparatus of claim 1 further comprising the sample container that is selected from a group consisting of: a test tube, a microtube, a PCR tube, and a cuvette.

7. The apparatus of claim 1 further comprising the magnetic particle within said sample container that is selected from a group consisting of: one or more permanently-magnetized magnetic particles, ferromagnetic particles, paramagnetic particles, diamagnetic particles, iron oxide nanoparticles, or other particles experiencing a motive force upon influence by an electromagnetic field.

8. An apparatus for tissue lysis under electromagnetic field control comprising:

a generalized toroidal sample container enclosing one or more magnetic particles along with a tissue sample;

a coil assembly arranged and configured around at least a portion of an outer surface of said sample container, said coil assembly comprising at least one electromagnetic coil, the at least one electromagnetic coil defining an outer coil surface and interior space disposed inwardly of the outer coil surface extending from a first end of the coil to an opposing second end, wherein at least a portion the generalized toroidal sample container is disposed within the interior space and extends from at least the first end to at least the second end of each coil, the at least one electromagnetic coil configured to generate a magnetic field upon excitation by an electrical current in the range of 10 to 900 amperes while limiting a variation in an ambient temperature at the coil assembly of less than or equal to 1 degree Celsius during generation of the magnetic field, said magnetic field proximate the internal volume of said generalized toroidal sample container;

a switching circuit comprising an electrical switching device for controlling said electrical current;

a processor electrically coupled to said switching circuit capable of activating said electrical switching device in a prescribed time-varying fashion;

a waveform generator interposed between said processor and said switching circuit, said waveform generator operable to provide said switching circuit with a prescribed time-varying current waveform upon direction by said processor, wherein said prescribed time-varying current waveform results in the magnetic field having a magnitude of 500 gauss to 50,000 gauss; and, a power source configured to deliver electrical voltages and currents to said processor, switching circuit, and electromagnetic coils.

9. The apparatus of claim 8 further comprising at least one sensor component, said sensor component suitable for detection and quantification of a physical parameter proximate said generalized toroidal sample container, wherein said sensor component is selected from a group consisting of: a solid-state magnetic field sensor, a Hall-effect sensor, a piezoelectric sensor, a vibration sensor, and an electromagnetic sensing coil.

10. The apparatus of claim 9 further comprising a feedback circuit interposed between said sensor component and said processor, said feedback circuit configured to optimize operating efficiency of said apparatus.

11. The apparatus of claim 8 wherein said magnetic particle within said sample container is selected from a group consisting of one or more permanently-magnetized magnetic particles, ferromagnetic particles, paramagnetic particles, diamagnetic particles, iron oxide nanoparticles, or other particles experiencing a motive force upon influence by an electromagnetic field.

12. The apparatus of claim 1 wherein a sample chamber is generally toroidal.

13. The apparatus of claim 1 further comprising at least one temperature sensor component suitable for detection and quantification of the ambient temperature at the coil assembly.

14. The apparatus of claim 8 further comprising at least one temperature sensor component suitable for detection and quantification of the ambient temperature at the coil assembly.

15. An apparatus for tissue lysis under electromagnetic field control comprising:

a generalized toroidal sample container enclosing one or more magnetic particles along with a tissue sample;

a coil assembly arranged and configured around at least a portion of an outer surface of said sample container, said coil assembly comprising at least one electromagnetic coil, the at least one electromagnetic coil defining an outer coil surface and interior space disposed inwardly of the outer coil surface extending from a first end of the coil to an opposing second end, wherein at least a portion of the toroidal sample container is disposed within the interior space and extends from at least the first end to at least the second end of each coil, the at least one electromagnetic coil configured to generate a magnetic field upon excitation by an electrical current from 10 amperes to 900 amperes while limiting a variation in an ambient temperature at the coil assembly of less than or equal to 1 degree Celsius during generation of the magnetic field, said magnetic field proximate the internal volume of said generalized toroidal sample container;

a switching circuit comprising an electrical switching device for controlling said electrical current;

a processor electrically coupled to said switching circuit capable of activating said electrical switching device in a prescribed time-varying fashion;

a waveform generator interposed between said processor and said switching circuit, said waveform generator operable to provide said switching circuit with a prescribed time-varying current waveform upon direction by said processor, wherein said prescribed time-varying current waveform results in the magnetic field having a magnitude of 500 gauss to 50,000 gauss;

at least one temperature sensor component suitable for detection and quantification of the ambient temperature at the coil assembly and, a power source configured to deliver electrical voltages and currents to said processor, switching circuit, electromagnetic coils and temperature sensor.

16. The apparatus of claim 15 further comprising at least one magnetic field sensor component in proximity to the at least one electromagnetic coil and electrically coupled to said processor, the at least one magnetic field sensor component suitable for detection and quantification of the magnetic field.

17. The apparatus of claim 15 further comprising at least one piezoelectric sensor in proximity to the at least one electromagnetic coil and electrically coupled to said processor.

18. The apparatus of claim 15 further comprising at least one vibration sensor in proximity to the at least one electromagnetic coil and electrically coupled to said processor.

* * * * *